United States Patent [19]

Rosenbluth et al.

[11] 4,323,072
[45] Apr. 6, 1982

[54] CANNULA FOR A VEIN DISTENTION SYSTEM

[75] Inventors: Robert F. Rosenbluth, Laguna Niguel, Calif.; Lawrence I. Bonchek, Milwaukee, Wis.

[73] Assignee: Shiley, Incorporated, Irvine, Calif.

[21] Appl. No.: 147,847

[22] Filed: May 8, 1980

Related U.S. Application Data

[62] Division of Ser. No. 113,247, Jan. 18, 1980.

[51] Int. Cl.³ ............ A61M 25/00; A61B 19/00
[52] U.S. Cl. .................... 128/348; 128/1 R; 128/221; 128/239; 128/747
[58] Field of Search ............... 128/214.2, 214.4, 221, 128/348, 349 R, 350, 239, 240, 242, 246, 341, 343, 344, 747, 1 R

[56] References Cited

U.S. PATENT DOCUMENTS

| | | | |
|---|---|---|---|
| 691,698 | 1/1902 | Eddy et al. | 128/239 |
| 777,182 | 12/1904 | Clarke | 128/240 |
| 1,316,394 | 9/1919 | Sellar | |
| 1,541,615 | 6/1925 | Bessesen | |
| 1,869,443 | 8/1932 | Stocklin | |
| 1,879,249 | 9/1932 | Honsaker | 128/239 |
| 1,998,225 | 4/1935 | Dow | 128/349 R |
| 2,291,191 | 7/1942 | Scudder, Jr. | 128/242 X |
| 2,630,805 | 3/1953 | Brehm | 128/242 |
| 2,646,042 | 7/1953 | Hsi hu | |
| 2,828,744 | 4/1958 | Hirsch et al. | 128/221 |
| 2,904,045 | 9/1959 | Owings | 128/221 |
| 3,082,769 | 3/1963 | Palmer | 128/221 |
| 3,358,684 | 12/1967 | Marshall | 128/348 X |
| 3,407,817 | 10/1968 | Galleher, Jr. | |
| 3,543,751 | 12/1970 | Sheffer | |
| 3,543,759 | 12/1970 | McWhorter | |
| 3,599,620 | 8/1971 | Balin | |
| 3,625,199 | 12/1971 | Summers | |
| 3,642,005 | 2/1972 | McGinnis | |
| 3,794,043 | 2/1974 | McGinnis | |
| 3,916,874 | 11/1975 | Perrin | |
| 3,958,557 | 5/1976 | Sharp et al. | 128/348 X |
| 4,000,741 | 1/1977 | Binard et al. | |
| 4,135,494 | 1/1979 | Stoner et al. | |

FOREIGN PATENT DOCUMENTS

| | | | |
|---|---|---|---|
| 1027322 | 5/1953 | France | 128/348 |
| 345490 | 1/1937 | Italy | 128/343 |
| 353564 | 10/1937 | Italy | 128/221 |
| 970647 | 9/1964 | United Kingdom | 128/349 |

Primary Examiner—Steven A. Bratlie
Attorney, Agent, or Firm—Knobbe, Martens, Olson, Hubbard & Bear

[57] ABSTRACT

A cannula used in the distention and irrigation of a saphenous vein which is being tested prior to use as a coronary or peripheral bypass graft includes a tapered and beveled tip which allows easy insertion into the vein, and a sloping shoulder just proximal to the tip which provides a convenient site for firmly securing the vein to the cannula with a ligature. The cannula can be utilized in a distention and irrigation apparatus which includes a pressure limiting device having a resilient membrane reservoir which limits static pressure delivered to the vein to a predetermined level. The device is connected between the cannula of the present invention and a syringe filled with irrigation fluid.

1 Claim, 6 Drawing Figures

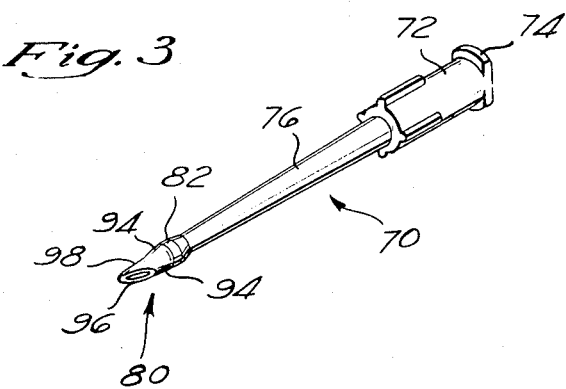
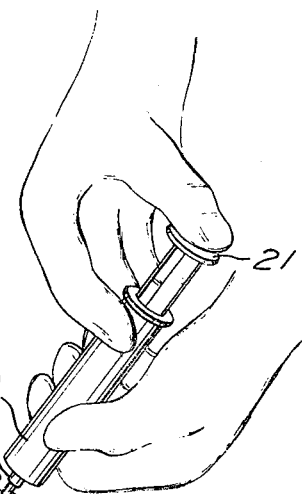
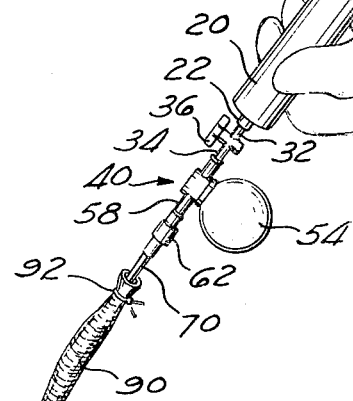
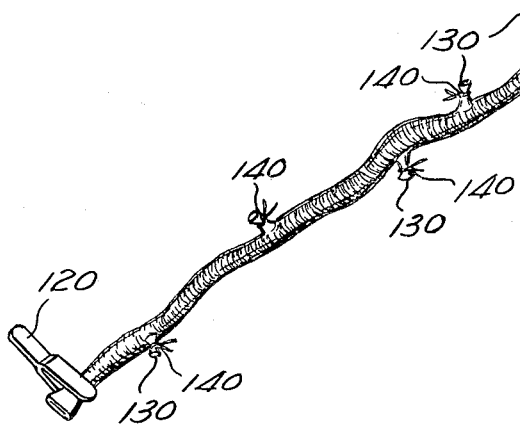

CANNULA FOR A VEIN DISTENTION SYSTEM

RELATED APPLICATION

This is a divisional of application Ser. No. 113,247, filed Jan. 18, 1980, entitled "Vein Distention System."

BACKGROUND OF THE INVENTION

This invention relates to a cannula utilized in an apparatus for the distention and irrigation of veins in preparation for transplantation within the human body. In particular, it relates to a cannula having an obliquely beveled tip for easy insertion of the cannula into the vein and a sloping shoulder for firm retention of the cannula in the vein.

The use of autogenous vein grafts in arterial bypass surgery has become a well-known procedure in the treatment of degenerative disorders in the coronary circulation system, and the saphenous vein in the leg is the preferred candidate for these grafts.

In the preparation of the vein segment for the grafting procedure, it is necessary to distend the vein segment after removal from the patient's leg in order to overcome spasm and to identify leaky side branches. Typically, this is done by tying off the upstream end of the vein segment and injecting irrigation fluid (typically a saline solution) into the open downstream end manually by means of a syringe. The typical procedure is described in some detail in U.S. Pat. No. 3,958,557 to Sharp, et al.

It has become known in recent years that distention of the veins at pressures in excess of 500 millimeters of mercury (mm Hg) can damage the vascular endothelium, with a resultant premature loss of vein patency subsequent to the bypass implantation. Thus, it has been established that excessive pressurization during distention can ultimately result in premature failure of the grafted vein segment due to thrombosis, subendothelial hyperplasia, or accelerated atherosclerosis.

Consequently, extreme care must be taken in the distention procedure to avoid excessive pressurization. Until recently, the degree of success achieved in this regard depended solely upon the judgment and skill of the operator performing the procedure. However, it was found that even the most skillful practitioner could not readily detect the relatively high pressures (600 to 700 mm Hg) generated by the syringe, because a vein in spasm has a small diameter and a low wall tension (Laplace's Law).

Thus, it has become apparent that some means is necessary for reliably limiting the distention pressure to a value below 500 mm Hg. In addition, recent experiments have demonstrated that distention pressures in the range of 100 to 400 mm Hg are necessary both to overcome spasm in most veins, and to reveal reliably all unsecured side branches in the vein segments involved. In some cases, static pressures of 400 mm Hg have been found to facilitate complete vein dilation, and transient pressures particularly spastic vein segments. The experiments demonstrated that static pressures as high as 500 mm Hg have been used to dilate particularly spastic vein segments. The experiments demonstrated that static pressures in the range of 100 to 400 mm Hg were well tolerated, producing little, if any, noticeable vein damage.

The results of these experiments indicated the need to provide static distention pressures in the range of 100 to 400 mm Hg, with the further need to allow transient pressures up to, but not substantially in excess of, 500 mm Hg. As previously noted, such static pressures allow substantially complete identification of all unsecured side branches. These side branches are preferably secured during the irrigation procedure, to ensure that none are overlooked.

In the prior art, continuous pressure must, typically, be supplied by the syringe. Thus, the person performing the distention procedure is not able, simultaneously, to secure the side branches, and an additional practitioner is necessary to perform this latter operation. Accordingly, it is desirable to have some means for automatically delivering the irrigation fluid, at the desired pressure, without the continued need for the syringe, thereby allowing a single practitioner first to initiate the irrigation, and then to secure the side branches while the irrigation continues under automatically controlled pressure.

The prior art has taught the desirability of injecting the irrigation fluid into the vein through a cannula inserted into the open end of the vein and secured thereto by a temporary ligature. One such cannula is disclosed in the aforementioned patent to Sharp et al. It has become the usual practice to cannulate the open upstream end of the saphenous vein before the downstream end is removed from the patient's leg. The open end of the vein remains cannulated throughout the irrigation and distention operation, until just before implantation of the vein segment as a coronary bypass. In this manner, the cannula provides easy identification of the respective ends of the vein, an important consideration since the valves in the vein allow blood flow in only one direction.

The typical prior art cannula has a blunt, circular leading edge on its tip, which is normally tapered to have an outside diameter at the leading edge which is approximately equal to the undistended inside diameter of the vein. The cannula may also include a peripheral flange to facilitate a temporary fluid-tight ligation of the vein on the cannula. It has been found that the blunt, circular leading edge of such a cannula is very difficult to insert into the vein, making this maneuver tedious and unnecessarily prolonged.

SUMMARY OF THE INVENTION

Broadly, the present invention is a specially configured cannula for attachment to a standard irrigation syringe. The cannula is advantageously utilized in a distention and irrigation system which includes a pressure-limiting device having a fluid inlet portion for receiving irrigation fluid from the syringe, a fluid outlet portion, and a resilient, balloon-like, bulbous reservoir in fluid communication with both the inlet and outlet portions. This distention system is described and claimed in more detail in an application entitled "Vein Distention System," Ser. No. 113,247, filed Jan. 18, 1980.

Detachably connected between the inlet portion of the pressure-limiting device and the outlet nozzle of the syringe is a short tubular section having a stopcock, and detachably connected to the outlet portion of the pressure-limiting device is the cannula of the present invention, having a tapered and beveled distal end or tip which provides both easy insertion into the open proximal end of the saphenous vein, and secure retention in the vein during the distention procedure.

The material, configuration, and dimensions of the resilient reservoir of the pressure-limiting device are selected so that the reservoir inflates within a specified range of pressures when it is filled with the contents of the syringe. This expansion of the reservoir assures that the hydrostatic pressure applied to the vein through the cannula cannot exceed the peak pressure attained in this pressure range. Thus, if excessive force is applied to the syringe, the reservoir begins to inflate, and the pressure transmitted to the vein cannot exceed the predetermined limit set by the expansion of the reservoir. In keeping with the clinical findings noted earlier, the reservoir is selected to have a predetermined inflation pressure of somewhere in the range of 100 to 400 mm Hg, depending upon the needs or preferences of the operator.

The use of the stopcock allows a controlled, substantially constant-pressure flow of fluid to be delivered to the vein without the need for the operator constantly to apply pressure to the syringe. To accomplish this, the reservoir is first pressurized by filling it with the entire contents of the syringe (after the vein has been "primed" with fluid). The stopcock is then closed, and the reservoir delivers fluid to the vein at the desired pressure automatically, without further need of the syringe. The operator now has both hands free to control the unsecured side branches of the vein, and manually to compress specific vein segments to treat localized areas of persistent spasm.

Although this pressure-limiting device can be used with standard vein irrigation cannulae, it is most advantageously used as a system with the specially-configured cannula of the present invention, designed to achieve easy insertion into the open, proximal end of the saphenous vein without unnecessary injury thereto, while at the same time providing secure retention within the venous lumen.

That is, the ease of insertion and secure retention of the present cannula substantially reduces the amount of handling of the vein required, thereby reducing the possibility of trauma to the vein. Even more importantly, the surgeon's time is saved—and frustration is avoided in completing the irrigation and distention process.

These advantages are achieved with a design in which the distal end or tip of the cannula is tapered down slightly from an outside diameter approximately equal to the undistended inside diameter of the vein, and which is obliquely beveled to present a narrow, arcuate (rather than circular) leading edge. The cannula is further provided with a gently-sloping shoulder just proximally of the tip. This shoulder provides a convenient site for a temporary fluid-tight ligation of the vein upon the cannula.

Thus, the cannula of the present invention is advantageously utilized in a system for saphenous vein distention and irrigation which substantially eliminates the two major causes of vein trauma which plagued the prior art: over-pressurization, and non-subtle cannulation. Moreover, this system provides optimal distention pressures for spasm elimination and leak detection, while allowing the operator to have both hands free to secure leaky side branches and to manipulate manually overly spastic portions of the subject vein segment.

BRIEF DESCRIPTION OF THE DRAWINGS

FIG. 3 is a perspective view of the cannula of the present invention;

FIG. 4 is a perspective view of a saphenous vein being irrigated and distended by use of the vein distention system;

DETAILED DESCRIPTION OF THE INVENTION Structure of the Overall System

Figure 1:
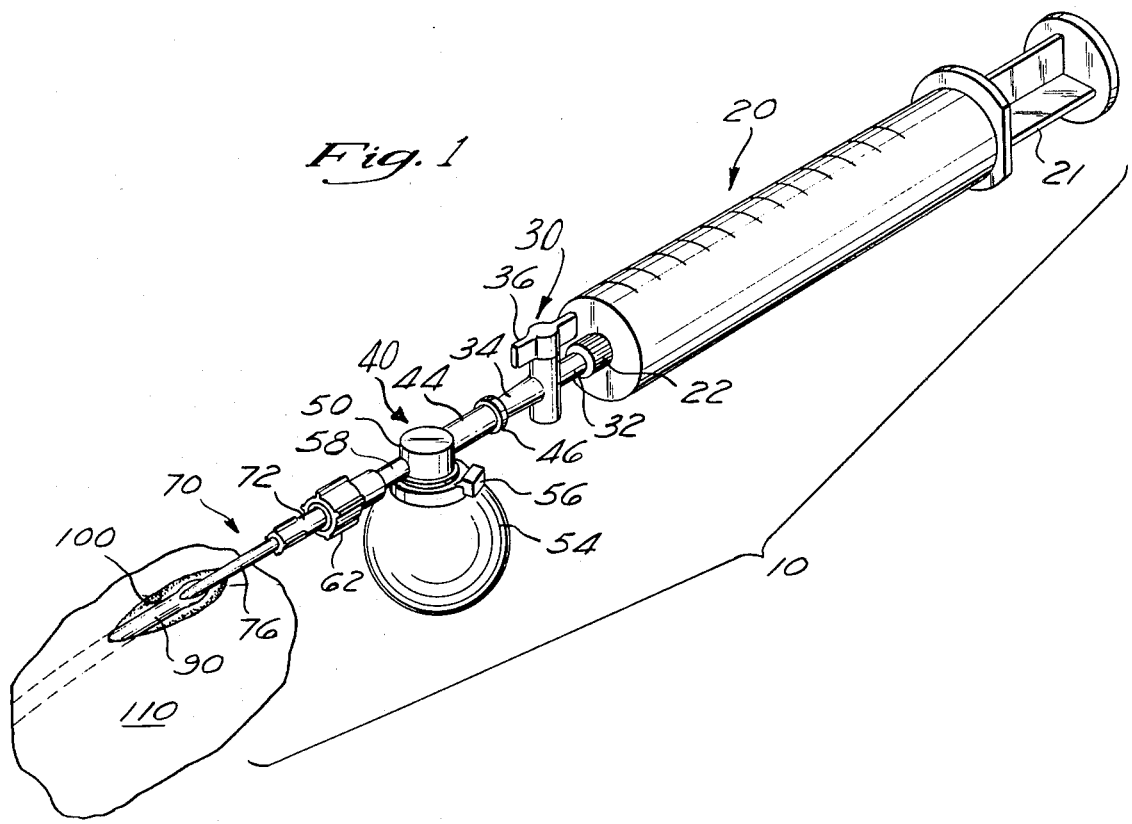
FIG. 1 is a perspective view of a vein distention system in position upon cannulation of the saphenous vein of a patient.

Referring just to FIG. 1, a vein distention and irrigation system 10 in accordance with the invention is shown. The major components of the system are a syringe 20, a valving member 30, a pressure-limiting device 40, and a cannula 70.

They syringe 20 is a typical disposable surgical syringe, preferably having a fluid capacity of about 60 cc. The syringe 20 has a plunger 21, and should be of the type having a Luer-lock nozzle 22, to provide a secure, fluid tight connection to the valving member 30.

The valving member 30 comprises basically a hollow tubular member having an inlet 32 adapted for connection to the Luer-lock nozzle 22 of the syringe 20, and an outlet 34. Between the inlet 32 and the outlet 34 is a stopcock 36 for opening and closing the passage (not shown) between the inlet 32 and the outlet 34.

Figure 2:
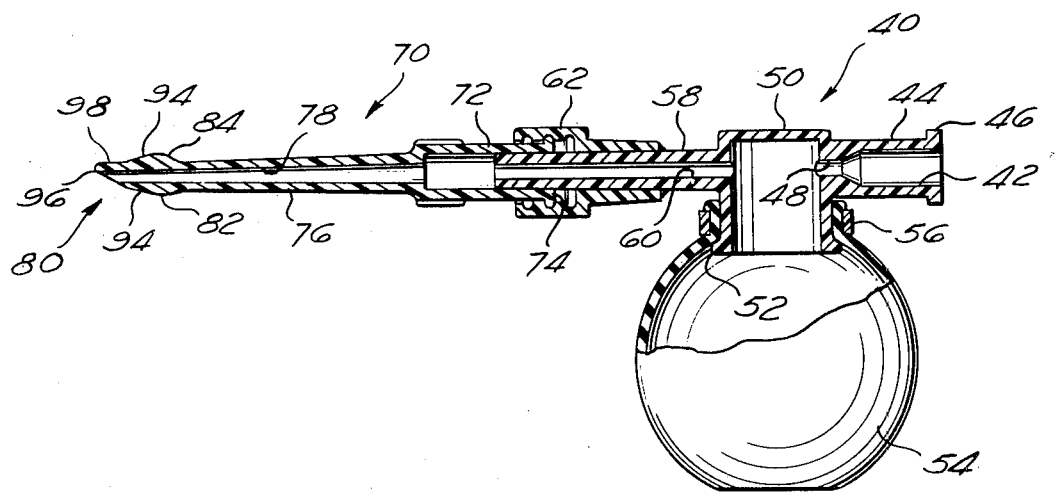
FIG. 2 is a cross-sectional view of the cannula of the present invention and the pressure-limiting device used in conjunction therewith.

The outlet 34 of the valving member 30 is slightly tapered to facilitate insertion into the bore 42 of an inlet section 44 of the pressure-limiting device 40. As best shown in FIG. 2, the inlet section 44 is advantageously provided with a peripheral flange 46 so that the pressure-limiting device 40 can be attached directly to the syringe 20 by means of the Luer-lock 22, if it is desired to do without the valving member 30.

Referring now to FIG. 2, the bore 42 of the inlet section communicates, via a reduced diameter passage 48, with a substantially cylindrical vertical chamber 50 which is open at one end (the bottom, as shown in FIG. 2). Surrounding the open (bottom) end of the chamber 50 is a peripheral lip or flange 52.

Secured over the open end of the chamber 50 around the flange 52 is a balloon-like, expandable reservoir 54, made of a resilient material, preferably latex. The reservoir 54 may be attached to the chamber 50 by means such as a nylon tie 56 as shown, or it may be glued or bonded directly to the chamber 50. The functional characteristics of the reservoir 54 will be discussed in detail below.

Extending from the side of the chamber 50 opposite the inlet section 44 is a tubular outlet section 58 having a central passage 60 communicating with the interior of the chamber 50. Attached to the distal (i.e., away from the syringe 20) end of the outlet section 58 is a Luer-lock fitting 62.

While the pressure-limiting device may be made of any number of materials, the inlet section 44, chamber 50, and outlet section 58 are preferably made as an integral unit of a rigid plastic material. An excellent example is a polycarbonate resin plastic such as that marketed under the trade name Lexan by General Electric Corporation. This material is rigid, easily formed, inexpensive, and naturally transparent, making it most suitable for a disposable unit.

The proximal (toward the syringe) portion of the cannula 70 comprises a tubular female fitting 72 adapted to receive the distal end of the outlet section 58 of the pressure-limiting device 40. The proximal end of the fitting 72 is provided with a peripheral flange 74 adapted to be lockably engaged in the Luer-lock fitting 62. (See FIG. 2).

Figure 6:
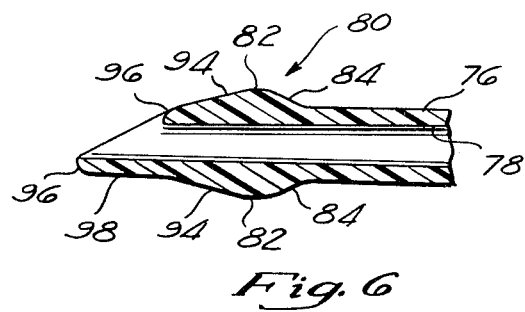
FIG. 6 is a longitudinal cross-sectional view of the tip of the cannula of the present invention.

The major novelty of the cannula resides in its specially configured tip 80, shown in FIGS. 2, 3, and 6. The proximal end of the tip 80 slopes radially outwardly at an angle of between about 20 degrees and 30 degrees (25 degrees optimally) to form a rounded peripheral ridge 82 around the exterior of the tip 80. The outside diameter of the ridge 82 is preferable approximately equal to, or slightly larger than, the nominal undistended inside diameter of a typical vein graft, so that the cannula, once inserted into the venous lumen, is retained therein. The sloping proximal side of the ridge thus forms a shoulder 84 (FIGS. 2 and 6) which provides a convenient site for tying the open upstream end of a saphenous vein segment (designated by the numeral 90 in FIG. 4) to the cannula 70 by means of a temporary ligature 92, to provide a fluid-tight seal.

Distally from the ridge 82, the tip 80 has a slightly tapered portion 94, which tapers radially inwardly at an angle of between about 7 degrees and 15 degrees (11 degrees optimally). This tapered section 94 is terminated on one side of the tip 80 by the proximal side of an oblique or beveled leading edge 96. The diametrically opposite side of the tapered section 94 is terminated by an untapered, axially-extending section 98 which extends to the distal side of the leading edge 96. Thus, as best shown in FIGS. 3 and 6, the cross-sectional shape of the leading edge rather than being circular, is a relatively narrow, arcuate or rounded "point," permitting easy insertion of the cannula into the open upstream end of the vein 90 (FIGS. 1 and 4) with minimal damage to the vein wall tissue.

The cannula 70 is preferably an integral unit of a plastic, such as poly(ethylene terephthalate) copolyester sold by Eastman Kodak. It should be noted that the tip 80 has no sharp corners or edges, either between the various sections described above or along the leading edge 96, all such corners and edges being rounded. Such a design thus significantly facilitates insertion of the cannula. Moreover, since the ligature site is the sloping shoulder 84, rather than a ridge or flange as in the prior art, the vein can be securely tied to the cannula.

Description of Function and Method of Use

As in the prior art, the harvesting of a segment of the great saphenous vein using the present invention begins with making an incision 100 in the leg 110 of a patient to expose the lower or upstream end of the great saphenous vein 90. (See FIG. 1.) The incision severs the upstream end of the vein, leaving it open for the insertion of the cannula 70. The cannula is inserted at this early stage, prior to removal of the vein from the patient's leg, so that the upstream end of the vein is clearly designated throughout the procedure, thereby allowing the vein to be oriented properly when it is grafted as an arterial bypass, since the valves in the vein allow fluid flow in only one direction. A segment of the vein 90, of the required length, may then be removed by extending the incision 100 upwardly along the patient's thigh.

The syringe 20 is filled with approximately 50 to 60 cc of irrigation fluid. Typically, this fluid has been a saline solution, but recently it has become the preferred practice to use the patient's own blood, or a mixture of blood and albumin, as the irrigation fluid in view of recent findings that saline solutions tend to cause a decrease in the fibrinolytic activity of the venous endothelium. Some practitioners nevertheless prefer a clear irrigation fluid, and where such a fluid is desired, a colloidal solution having an oncotic pressure and pH similar to human blood should be chosen. One acceptable example is a 5% solution of albumin in a balanced electrolyte solution with normal pH.

With the valving assembly 30 and the pressure limiting device 40 attached to the syringe 20 as shown, a portion of the irrigation fluid in the syringe is injected into the valving assembly 30 and the pressure limiting device 40, with the nozzle 22 of the syringe held upwardly at about a 45 degree angle, the resilient reservoir 54 oriented downwardly, and with the stopcock 36, of course, open. This portion of the fluid (approximately 15 cc when a reservoir of the dimensions given below is used) should be sufficient to fill completely the valving member 30 and the pressure-limiting device 40, including the reservoir 54.

Thus primed, the syringe/valving member/pressure-limiting device assembly is attached to the cannula 70 which has been inserted into the upstream end of the harvested vein segment, as previously described. The vein segment is now irrigated to flush out any occlusions or blood clots, by injecting a small amount of irrigating flush into the vein. After flushing is completed, the open downstream end of the vein segment is closed, for example with an atraumatic surgical clamp 120 (FIG. 4) and the vein, completely or at least partially filled with fluid, is now prepared for distention.

As the vein segment is filled with irrigation fluid, the pressure within the vein rises. If the force or pressure applied to the syringe plunger is carefully controlled, the pressure within the vein will not exceed that which is necessary to overcome spasm and to detect leaky side branches (designated by the numeral 130 in FIG. 4) which are then tied off or secured by ligature 140.

However, as previously mentioned, it is normally very difficult for the operator to know when a safe hydrostatic pressure level in the vein segment has been exceeded via the application of excessive force to the syringe plunger. However, this problem is avoided through the use of the expandable reservoir 54 of the pressure-limiting device 40. This results from the fact that the balloon-like reservoir is specifically designed to expand or inflate when the pressure in the vein (transmitted to the reservoir 54 via the cannula 70) exceeds a predetermined maximum value. Thus, in one mode of operation of the pressure limiting device 40, the expansion of the resilient reservoir 54 serves as a warning indicator to the operator that the predetermined maximum pressure has been reached and that no more force should be applied to the plunger 21.

Even if the warning presented by the inflated reservoir 54 is ignored, and further pressure is applied to the plunger, the reservoir will continue to inflate without increasing the pressure in the vein segment. Thus, the pressure applied to the vein segment is limited to the maximum pressure required to inflate the reservoir. This maximum pressure is, of course, dependent solely upon the physical characteristics of the reservoir.

As previously noted, it has been shown that a distention pressure of between 100 and 400 mm Hg is usually necessary for effective elimination of vein spasm and revelation of leaky side branches. Thus, the characteristics of the reservoir can be selected so that the reservoir has a predetermined peak inflation pressure of somewhere between 100 and 400 mm Hg.

Figure 5:
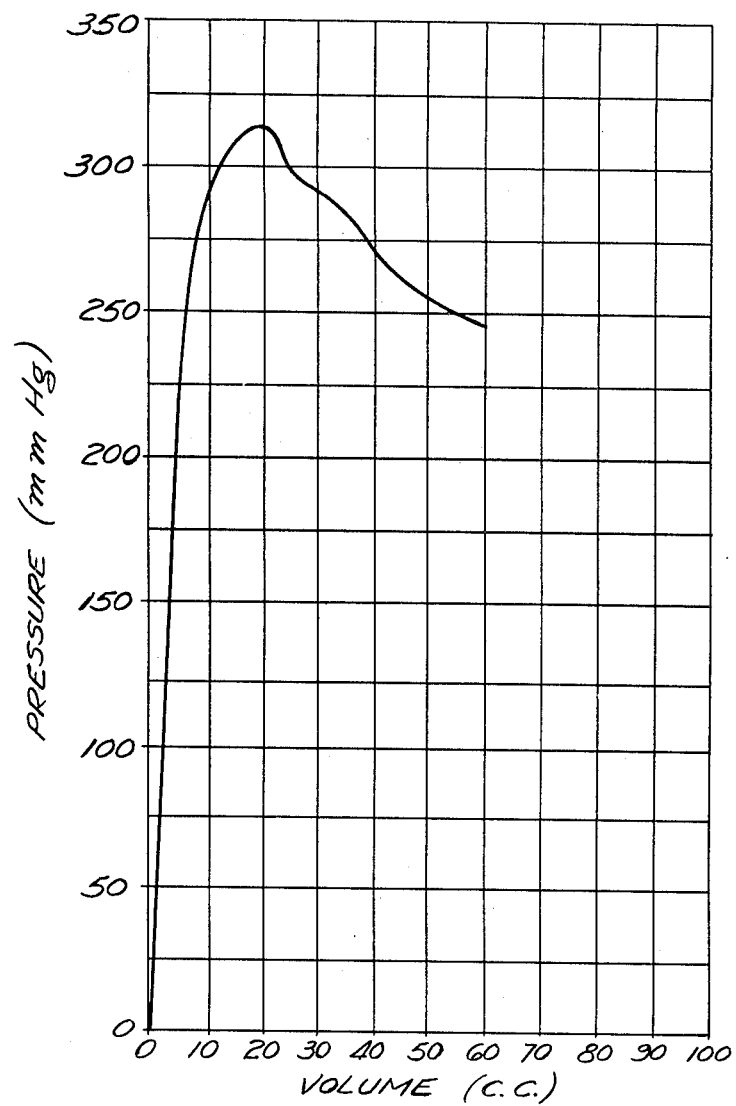
FIG. 5 is a graphical representation of typical pressure versus volume characteristics of the pressure-limiting device used with the cannula of the present invention.

By way of specific example, pressure versus volume curves for several representative prototypes of the pressure-limiting device were generated during experimental testing procedures, and the curve illustrated in FIG. 5 represents the average of these curves. It can be seen that for these particular prototypes a peak pressure of approximately 315 mm Hg was generated, on the average, and this pressure was reached when the reservoir was filled with approximately 20 cc of fluid. Further filling of the reservoir resulted in a decrease in pressure, so that when the reservoir was filled to the capacity of the syringe (i.e., about 60 cc) a pressure slightly less than 250 mm Hg was generated.

The reservoir used in these tests was approximately spherical, as shown in the drawings, with a maximum outside diameter of approximately 3.2 cm and a wall thickness of approximately 33 mils (0.84 mm). The composition of the reservoir was natural rubber latex, of the type marketed by B. F. Goodrich Company under the designation "Compound 60LA298B". The cured film physical properties of this compound are as follows:

| | |
|---|---|
| Tensile strength: | 4000–5000 psi |
| Tear strength: | 300–350 psi |
| Elongation (Elasticity): | 750–900% |

Should a peak pressure of approximately 400 mm Hg be desired, the wall thickness of the reservoir can simply be increased, the peak inflation pressure being roughly proportional to the wall thickness. Thus, it has been determined that a reservoir having dimensions and composition identical to those described above, except having a wall thickness of about 44 mils (1.1 mm) will exhibit a peak pressure of approximately 400 mm Hg, when the state of cure of the rubber is appropriately chosen and controlled.

It will be understood that the reservoirs providing other peak pressures in the range of 100 to 400 mm Hg can be constructed utilizing differing wall thicknesses and compositions and states of cure. Thus, it will be appreciated by those skilled in the art that a reservoir having the requisite pressure versus volume characteristics can be constructed from a variety of resilient, rubber-like materials, with the dimensions of the reservoir being dictated by the physical characteristics of the material and by the particular peak pressure desired.

The stopcock 36 in the valving assembly 30 allows the use of another mode of operation. In this procedure, after the vein has been irrigated and filled with irrigation fluid, the reservoir 54 is gradually filled and inflated with the remaining contents of the syringe while the pressure-limiting device is attached to the cannula in the vein. When the reservoir is fully inflated, the stopcock 36 is closed. The reservoir is now self-pressurized at a predetermined pressure (depending on the volume of fluid therein), and it will continually deliver fluid to the vein (through the cannula) at approximately this predetermined pressure, which will never exceed the predetermined peak pressure. Moreover, the fluid is delivered automatically, without the need for the continued application of force on the plunger of the syringe. Thus, the operator has both hands free to tie off unsecured side branches.

As previously mentioned, complete dilation of the vein may require momentary pressures in excess of 400 mm Hg. Such transient pressures can be achieved by intermittently squeezing the reservoir, preferably with the stopcock closed. In addition, localized areas of persistend spasm can be distended, without subjecting the entire vein to excessive pressure, by digitally compressing the vein on both sides of the involved segment, and "milking" the entrapped fluid centispetally toward the center. This transiently raises the pressure in the affected segment only as high as necessary to overcome spasm, and the pressure is released as soon as the vein dilates. Again, this procedure is preferably performed with the stopcock closed, so that the operator has both hands free to perform the "milking" while fluid is continuously delivered to the vein under controlled pressure.

From the foregoing description of the invention and its manner of use, it will be appreciated that the invention offers the advantages of safe, quick, essentially non-traumatic cannulation, with good cannula retention within the vein. The net results of these advantages are (a) a dramatic increase in the speed and safety with which the vein can be prepared for grafting; and (b) a substantially diminished risk of premature loss of patency in the grafted vein, with a resultant increase in the success rate of the arterial bypass or other procedure using the venous graft.

What is claimed:

1. A cannula for use in testing a saphenous vein as a coronary or peripheral bypass graft, said cannula comprising:
    a conduit for communicating fluid to said vein; and
    a flat, elongate tip on the distal end of said conduit comprising:
        a distal beveled portion having generally rounded edges;
        a non-tapered section on the side of said tip opposite said beveled portion, said beveled portion and said non-tapered section providing means for forming a generally arcuate leading edge on said tip for facilitating insertion of said tip into said vein and preventing damage to vein tissue;
        a tapered portion having a taper of about 7 to 15 degrees located proximally with respect to said beveled portion, said tapered portion forming a ridge to provide means for retaining said cannula within said vein; and
        a shoulder having a taper of about 20 to 30 degrees located proximally with respect to and tapered in an opposite direction as said tapered portion to provide means for facilitating a sealing ligature around said vein.

* * * * *